US010428013B2

(12) United States Patent
Yu et al.

(10) Patent No.: US 10,428,013 B2
(45) Date of Patent: Oct. 1, 2019

(54) AMIDE COMPOUND, PREPARATION METHOD AND USES THEREOF

(75) Inventors: Zhenpeng Yu, Shanghai (CN); Gouping Wang, Shanghai (CN); Zhen Zhang, Shanghai (CN); Minyu Liu, Shanghai (CN); Xiaoling Huang, Shanghai (CN); Ying Liu, Shanghai (CN); Lin Xiao, Shanghai (CN); Li Cai, Shanghai (CN); Xuejun Wu, Shanghai (CN); Yifang Deng, Shanghai (CN); Mianli Pan, Shanghai (CN); Renhai Chen, Shanghai (CN); Shenrong Tang, Shanghai (CN); Quanhai Liu, Shanghai (CN)

(73) Assignees: Shanghai Institute of Phamaceutical Industry, Shanghai (CN); China State Institute of Pharmaceutical Industry, Shanghai (CN)

(*) Notice: Subject to any disclaimer, the term of this patent is extended or adjusted under 35 U.S.C. 154(b) by 920 days.

(21) Appl. No.: 14/129,000

(22) PCT Filed: Jun. 25, 2012

(86) PCT No.: PCT/CN2012/077418
§ 371 (c)(1),
(2), (4) Date: Dec. 23, 2013

(87) PCT Pub. No.: WO2012/175049
PCT Pub. Date: Dec. 27, 2012

(65) Prior Publication Data
US 2014/0128463 A1 May 8, 2014

(30) Foreign Application Priority Data
Jun. 24, 2011 (CN) .......................... 2011 1 0174070

(51) Int. Cl.
*C07C 235/84* (2006.01)
*A61K 31/165* (2006.01)
*A61K 31/166* (2006.01)
*A61K 31/222* (2006.01)
*C07C 325/02* (2006.01)
*C07C 235/20* (2006.01)
*C07C 235/26* (2006.01)
*C07C 251/24* (2006.01)
*C07C 231/02* (2006.01)

(52) U.S. Cl.
CPC .......... *C07C 235/84* (2013.01); *A61K 31/165* (2013.01); *A61K 31/166* (2013.01); *A61K 31/222* (2013.01); *C07C 231/02* (2013.01); *C07C 235/20* (2013.01); *C07C 235/26* (2013.01); *C07C 251/24* (2013.01); *C07C 325/02* (2013.01); *C07C 2601/02* (2017.05); *C07C 2601/14* (2017.05)

(58) Field of Classification Search
CPC .. A61K 31/165; A61K 31/166; A61K 31/222; C07C 2101/02; C07C 2101/14; C07C 231/02; C07C 235/20; C07C 235/26; C07C 235/84; C07C 251/24; C07C 325/02
See application file for complete search history.

(56) References Cited

U.S. PATENT DOCUMENTS 3,439,018 A * 4/1969 Leafe .................... C07C 255/00
                                                            504/280
2010/0087543 A1   4/2010 Ebdrup et al.

FOREIGN PATENT DOCUMENTS

| CN | 101108173 A | 1/2008 |
|---|---|---|
| CN | 102093246 A | 6/2011 |
| GB | 832286 A * | 4/1960 |
| GB | 832289 A | 4/1960 |
| GB | 01041982 A | 9/1966 |
| JP | S60-258150 A | 12/1985 |
| JP | 2001-097957 A | 4/2001 |
| WO | 2006/016218 A1 | 2/2006 |
| WO | WO2006/016218 A1 * | 2/2006 |
| WO | 2008-134221 A1 | 11/2008 |
| WO | 2008/150486 A2 | 12/2008 |

OTHER PUBLICATIONS

International Search Report for corresponding International Application No. PCT/CN2012/077418, dated Oct. 4, 2012 (6 pages).
International Preliminary Report on Patentability for corresponding International Application No. PCT/CN2012/077418, dated Sep. 12, 2013 (19 pages).
N.M. Przheval'skii et al.; "Fischer Synthesis of 3-(N-Acylamino)-2-Phenylindoles;" Chemistry of Heterocyclic Compounds, vol. 38, No. 9; Sep. 2002; pp. 1055-1061 (7 pages).
Extended European Search report dated Jan. 20, 2015, in corresponding European Patent Application No. 12802606.9 (8 pages).
Japanese Office Action (Decision to Grant a Patent) dated Sep. 8, 2015, in corresponding Japanese Patent Application No. JP 2014-516180, with English translation (6 pages).
Chinese Office Action (Notification to Grant Patent Right for Invention) dated Nov. 9, 2015, in corresponding Chinese Patent Application No. 201110174070.5, with USPTO Global Dossier English translation (5 pages).
C. T. Fridman; Zhurnal Obshchei Khimii, vol. 25, 1955, pp. 970-975; XP009181690; ISSN: 0044-460X (7 pages).

* cited by examiner

*Primary Examiner* — Jean P Cornet
(74) *Attorney, Agent, or Firm* — Osha Liang LLP

(57) ABSTRACT

Disclosed are amide compounds, preparation method and uses thereof, specifically, the compounds represented by formula I or pharmaceutically acceptable salts, wherein $R_1$, $R_2$, $R_3$, $R_4$, $R_5$, Q, X and n are defined as in the description. Also disclosed are a method for preparing the compounds of formula I, a composition containing the compounds, and the uses of the same in the preparation of medicaments for regulating blood lipid and/or preventing gallstone. The compounds of formula I disclosed in the present invention have stability in vitro, good solubility in the pharmaceutical organic solvents and favorable bioavailability in animals.

3 Claims, No Drawings

AMIDE COMPOUND, PREPARATION METHOD AND USES THEREOF

FIELD OF THE INVENTION

The present invention relates novel amide compounds, and preparation method and use thereof, and in particular, to the amides made from amine compounds and carboxylic acid compounds, and the preparation method and use thereof.

BACKGROUND OF THE INVENTION

The cardio-cerebrovascular diseases are the most serious disorders currently endangering human life and health, which are common and frequent for the middle-aged and elderly people. In many countries, they are at the top in morbidity and mortality. Atherosclerosis contributes to a number of cardio-cerebrovascular diseases, and there are substantial evidences in laboratory and clinical data that atherosclerosis is closely associated with abnormal metabolism of blood lipid. Therefore, the medicaments for adjusting blood lipid represent an important field of current study on new medicament.

By forward, randomized and control clinical studies, it has been established that some statins enable reduced occurrence of atherosclerosis and coronary disease, lowering mortality caused by coronary disease and lowering incidence of myocardial infarction. Moreover, it has been further established that treatment with lipid-lowering drugs enables reduced lipid in atherosclerotic plaque and reinforced fiber lipid for stabilization of the plaque, leading to reduction of such severe events as myocardial infarction and cerebral infarction caused by plaque fracture. In addition, the medicaments for regulating blood lipid also enable the functions of the damaged vascular endotheliocyte to resume, enhance fibrinolysis, prevent thrombosis, and delay progression of atherosclerosis in human and remove the formed plaque. Therefore, it is an important approach for positive treatment with the blood lipid-regulating medicaments to reduce occurrence of atherosclerosis and coronary disease.

There are a variety of clinic and common medicaments for regulating blood lipid, for example HMG-CoA reductase inhibitors, phenoxy carboxylic acids, ion exchange resins orbile acid sequestrants, niacins and others. Among others, the statins (i.e. HMG-CoA reductase inhibitors) are particularly attractive.

The statins are the inhibitors of cholesterol synthetase. For conversion of HMG-CoA into mevalonic acid by the HMG-CoA reductase, the statins have an open acid moiety in the chemical structure similar as HMG-CoA, which is capable of competitively inhibiting formation of mevalonic acid, thus reducing synthesis of cholesterol, resulting in reduction of cholesterol and low-density lipoprotein (LDL-C) level in blood. There are further clinical studies showing that, in the patients with coronary disease even in which the cholesterol and low-density lipoprotein levels in sera are less high or normal, the stains are also capable of preventing occurrence, development of atherosclerotic plaque and reducing the severe clinic events such as coronary disease. However, for long-term dosing with the statins, in most of patients, impaired liver function, increased aminotransferases, muscular pain and increased creatine kinases will occur, in addition to such symptoms in digestive system as epigastric discomfort.

Therefore, there is an objective demand for constant development of new lipid-lowering drug with good efficacy and low side effects.

SUMMARY OF THE INVENTION

In the present invention, amine compounds and carboxylic acid compounds are linked by covalent bond of ester and amide, thus providing novel amide compounds with in vivo regulation of blood lipid and/or prevention from cholelithiasis. The compounds not only cause triglyceride in blood of the hyperlipoidemia animal model to decrease, but also favorably function for reduction of cholesterol and low-density lipoprotein, and have an effect of prevention from gallstone in gallstone model of golden hamster. Particularly, toxicity of the compounds provided by the present invention is low.

The first object of the present invention is to provide a compound represented by formula I or pharmaceutically acceptable salts thereof,

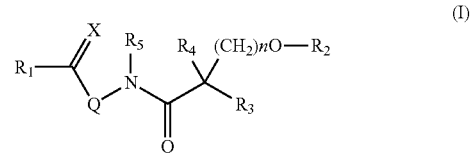

wherein:

$R_1$ is selected from phenyl, mono-substituted or poly-substituted phenyl, wherein the substituent on the phenyl is selected from halogen, hydroxy, $C_1$-$C_{10}$ alkyl, $C_1$-$C_{10}$ alkoxy, $C_3$-$C_{10}$ cycloalkyl, $C_1$-$C_{10}$ alkyl bearing $C_5$-$C_{10}$ aryl, $C_5$-$C_{10}$ aryl, 3-10-membered heterocyclic radical containing 1-3 heteroatoms independently selected from N, O or S, 5-10-membered heteroaryl containing 1-3 heteroatoms independently selected from N, O or S, substituted $C_1$-$C_{10}$ alkyl, substituted $C_3$-$C_{10}$ cycloalkyl, substituted formyl; or $R_1$ is selected from

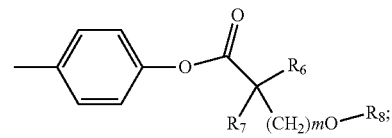

wherein $R_6$ and $R_7$ are independently selected from H or substituted or non-substituted $C_1$-$C_{10}$ alkyl, $C_3$-$C_{10}$ cycloalkyl;

$R_2$ and $R_8$ are independently selected from phenyl, mono-substituted or poly-substituted phenyl, wherein the substituent on the phenyl includes halogen, hydroxy, $C_1$-$C_{10}$ alkyl, $C_1$-$C_{10}$ alkoxy, $C_3$-$C_{10}$ cycloalkyl, $C_1$-$C_{10}$ alkyl bearing $C_5$-$C_{10}$ aryl, $C_5$-$C_{10}$ aryl, 3-10-membered heterocyclic radical containing 1-3 heteroatoms independently selected from N, O or S, 5-10-membered heteroaryl containing 1-3 heteroatoms independently selected from N, O or S, substituted $C_1$-$C_{10}$ alkyl, substituted $C_3$-$C_{10}$ cycloalkyl, substituted formyl;

$R_3$, $R_4$ and $R_5$ are independently selected from H or substituted or non-substituted $C_1$-$C_{10}$ alkyl, $C_3$-$C_{10}$ cycloalkyl;

Q is selected from linear, branched or cyclic $C_1$-$C_6$ alkylene;

X is selected from oxygen, sulfur or nitrogen;

m is an integer from 0 to 10; and n is an integer from 0 to 10;

The substituent is selected from halogen, $C_1$-$C_{10}$ alkyl, $C_3$-$C_{10}$ cycloalkyl, $C_1$-$C_{10}$ alkyl bearing $C_5$-$C_{10}$ aryl, $C_5$-$C_{10}$ aryl, 3-10-membered heterocyclic radical containing 1-3 heteroatoms independently selected from N, O or S, or 5-10-membered heteroaryl containing 1-3 heteroatoms independently selected from N, O or S, benzoyl or amido.

In a preferable embodiment according to the present invention, provided are the compounds represented by formula I or pharmaceutically acceptable salts thereof, wherein $R_1$ is selected from phenyl, mono-substituted or poly-substituted phenyl, wherein the substituent on the phenyl is selected from halogen, hydroxy, $C_1$-$C_6$ alkyl, $C_1$-$C_6$ alkoxy, $C_3$-$C_6$ cycloalkyl, $C_1$-$C_6$ alkyl bearing $C_5$-$C_{10}$ aryl, $C_5$-$C_{10}$ aryl, 3-10-membered heterocyclic radical containing 1-3 heteroatoms independently selected from N, O or S, 5-10-membered heteroaryl containing 1-3 heteroatoms independently selected from N, O or S, substituted $C_1$-$C_6$ alkyl, substituted $C_3$-$C_6$ cycloalkyl, substituted formyl; or $R_1$ is selected from wherein $R_6$ and $R_7$ are independently selected from H or substituted or non-substituted $C_1$-$C_6$ alkyl, $C_3$-$C_6$ cycloalkyl;

$R_2$ and $R_8$ are independently selected from phenyl, mono-substituted or poly-substituted phenyl, wherein the substituent on the phenyl is selected from halogen, hydroxy, $C_1$-$C_6$ alkyl, $C_1$-$C_6$ alkoxy, $C_3$-$C_6$ cycloalkyl, $C_1$-$C_6$ alkyl bearing $C_5$-$C_{10}$ aryl, $C_5$-$C_6$ aryl, 3-10-membered heterocyclic radical containing 1-3 heteroatoms independently selected from N, O or S, 5-10-membered heteroaryl containing 1-3 heteroatoms independently selected from N, O or S, substituted $C_1$-$C_6$ alkyl, substituted $C_3$-$C_6$ cycloalkyl, substituted formyl;

$R_3$, $R_4$, $R_5$, $R_6$ and $R_7$ are independently selected from H or substituted or non-substituted $C_1$-$C_6$ alkyl or $C_3$-$C_6$ cycloalkyl;

Q is selected from linear or branched $C_1$-$C_3$ alkylene;

X is selected from oxygen or nitrogen;

m is an integer from 0 to 8; and n is an integer from 0 to 8;

In a further preferable embodiment according to the present invention, provided are the compounds represented by formula I or pharmaceutically acceptable salts thereof, wherein $R_1$ is the mono-substituted or poly-substituted phenyl, wherein the substituent on the phenyl is characterized by having at least one hydroxy substituent;

$R_2$ and $R_8$ are independently selected from mono-substituted or di-substituted phenyl, wherein the substituent on the phenyl is halogen, $C_1$-$C_6$ alkyl or $C_1$-$C_6$ alkoxy;

$R_3$, $R_4$, $R_5$, $R_6$ and $R_7$ are independently selected from H or substituted or non-substituted $C_1$-$C_6$ alkyl;

Q is methylene;

X is oxygen;

m is an integer from 0 to 5; and n is an integer from 0 to 5;

In a particularly preferred embodiment according to the present invention, $R_1$ is p-hydroxyphenyl.

In a particularly preferred embodiment according to the present invention, $R_2$ and $R_8$ are 2,5-dimethylphenyl.

In a particularly preferred embodiment according to the present invention, $R_3$, $R_4$, $R_6$ and $R_7$ are methyl.

In a particularly preferred embodiment according to the present invention, m and n are 3.

In a particularly preferred embodiment according to the present invention, the halogen is chloride or bromide; $R_5$ is H.

In the particularly preferred embodiments according to the present invention, the compounds I of the present invention are those below:

01

02

-continued
03
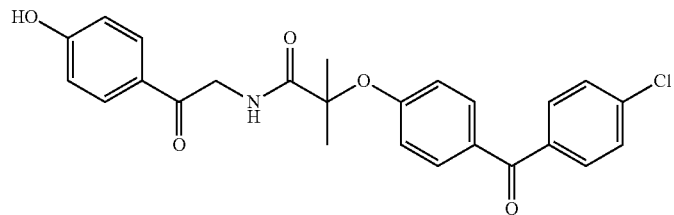
04
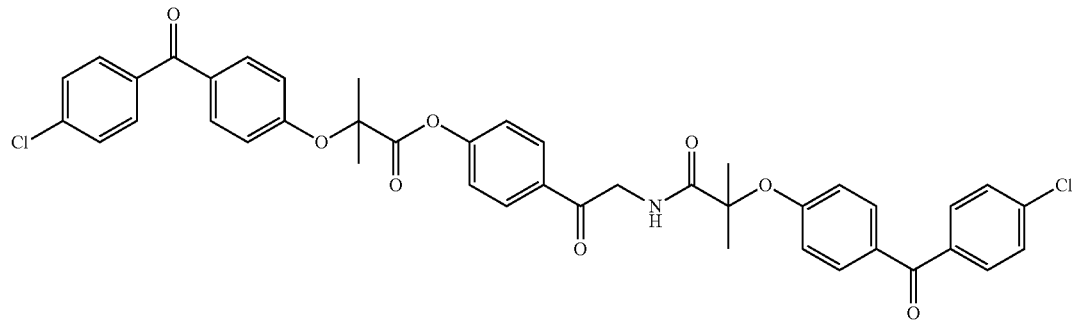
05
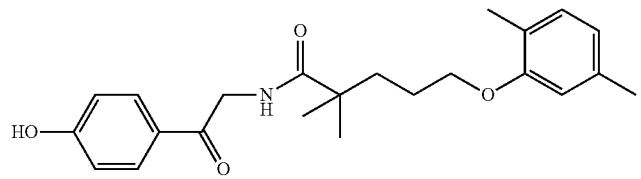
06
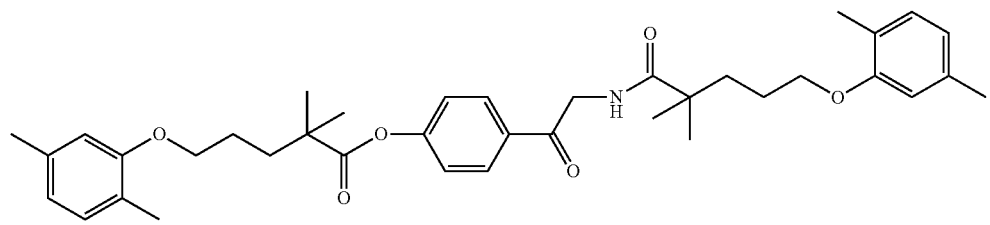
07
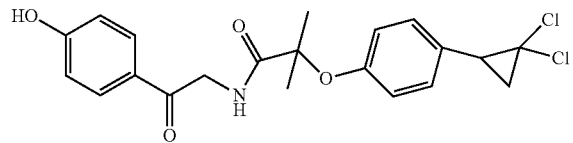
08
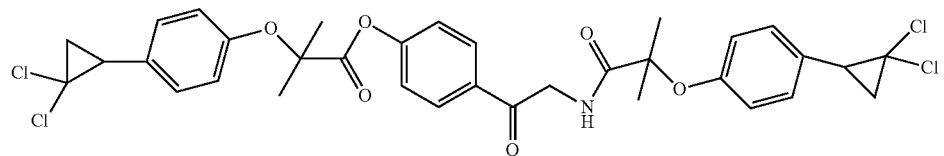
09 10
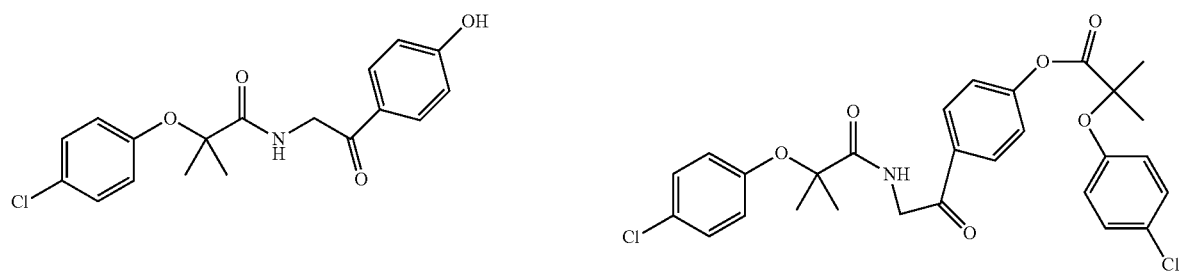

11
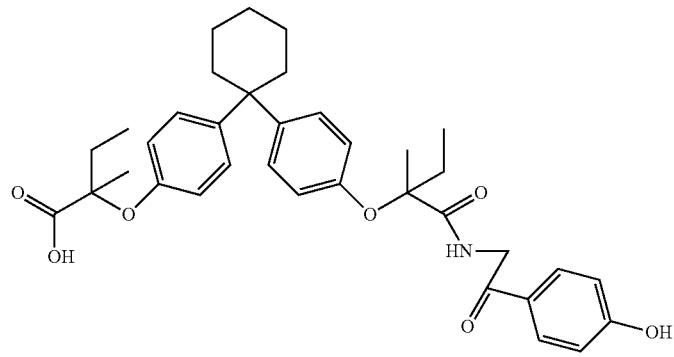
12
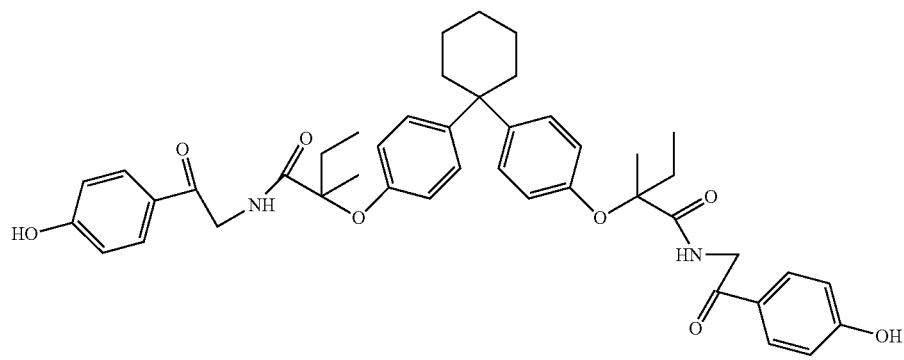
13
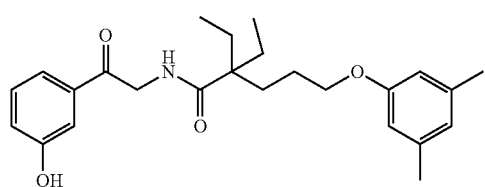
14
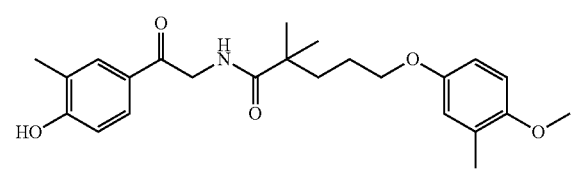
15
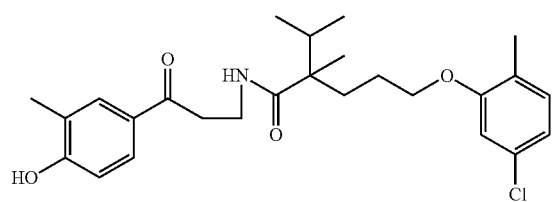
16
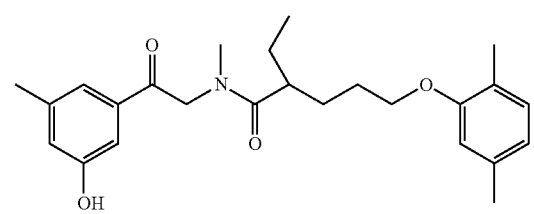
17
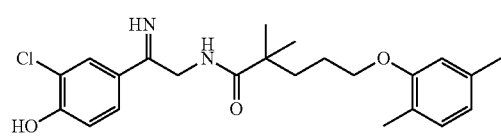
18
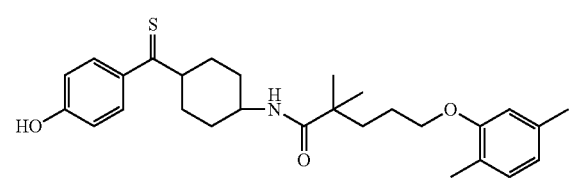
19
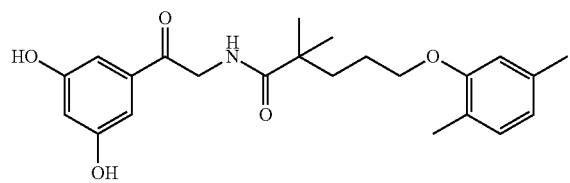
20
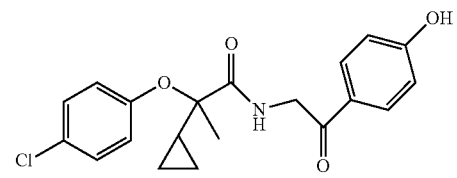

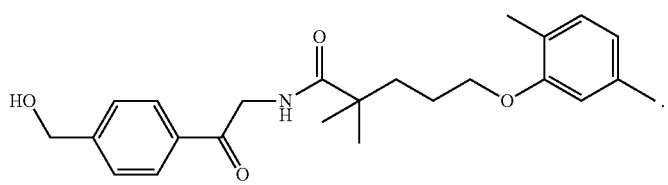

Unless otherwise stated, the following terms present in the description and claims of the present invention have the following meaning:

As used herein, "alkyl" refers to a branched or linear saturated aliphatic hydrocarbyl comprising a given number of carbon atoms. For example, as defined in "$C_1$-$C_{10}$ alkyl", $C_1$-$C_{10}$ includes those having 1, 2, 3, 4, 5, 6, 7, 8, 9 or 10 carbon atoms in linear or branch structure. For example, "$C_1$-$C_{10}$ alkyl" specifically includes methyl, ethyl, n-propyl, isopropyl, n-butyl, tert-butyl, isobutyl, pentyl, hexyl, heptyl, octyl, nonyl, decyl and the like.

The terms "cycloalkyl" refer to a mono-cyclic saturated aliphatic hydrocarbyl having a given number of carbon atoms. For example, "cycloalkyl" includes cyclopropyl, methyl-cyclopropyl, 2,2-dimethyl-cyclobutyl, 2-ethyl-cyclopentyl, cyclohexyl and the like.

The terms "alkoxy" refer to a cyclic or non-cyclic alkyl having the stated number of carbon atoms and bridged by oxygen. Thus, "alkoxy" encompasses the above definitions of alkyl and cycloalkyl.

The terms "alkenyl" refer to a linear, branched or cyclic non-aromatic hydrocarbyl comprising a given number of carbon atoms and at least one carbon-carbon double bond. Preferred is presence of one carbon-carbon double bond, and presence of up to four non-aromatic carbon-carbon double bonds is possible. For example, "$C_2$-$C_{10}$ alkenyl" refers to one having 2-10 carbon atoms. "$C_2$-$C_6$ alkenyl" refers to one having 2-6 carbon atoms, including ethenyl, propenyl, butenyl, 2-methylbutenyl and cyclohexenyl. The linear, branched or cyclic moieties on the alkenyl may comprise double bond, and where the substituted alkenyl is indicated, it may be substituted.

The terms "alkynyl" refers to a linear, branched or cyclic hydrocarbyl having a given number of carbon atoms and at least one carbon-carbon triple bond. Presence of up to three carbon-carbon triple bonds therein is possible. For example, "$C_2$-$C_{10}$ alkynyl" refers to one having 2-10 carbon atoms. "$C_2$-$C_6$ alkynyl" refers to one having 2-6 carbon atoms, including acetenyl, propinyl, butynyl, 3-methylbutynyl and the like.

The terms "cycloalkyl" refers to a saturated or partially unsaturated mono-cyclic, multi-cyclic or bridged carbocyclic substituent. For example, the ring having 3-20 carbon atoms may be expressed as $C_{3-20}$ cycloalkyl; the ring having 5-15 carbon atoms may be expressed as $C_{5-15}$ cycloalkyl; and the ring having 3-8 carbon atoms may be expressed as $C_{3-8}$ cycloalkyl, and the like. The terms include, but not limited to, cyclopropyl, cyclobutyl, cyclopentyl, cyclohexyl, cycloheptyl, cyclooctyl, 1H-indenyl, 2,3-dihydroindenyl, 1,2,3,4-tetrohydronaphthyl, 5,6,7,8-tetrahydronaphthyl, 8,9-dihydro-7H-benzocyclohepten-6-yl, 6,7,8,9-tetrohydro-5H-benzocycloheptenyl, 5,6,7,8,9,10-hexahydro-benzocyclooctenyl, fluorenyl, bicyclo[2.2.1]heptyl, bicyclo[2.2.1]heptenyl, bicyclo[2.2.2]octyl, bicyclo[3.1.1]heptyl, bicyclo[3.2.1]octyl, bicyclo[2.2.2]octylenyl, bicyclo[3.2.1]octylenyl, adamantanyl, octahydro-4,7-methylene-1H- indenyl, octahydro-2,5-methylene-pentalene and the like. The substituent on the cycloalkyl may be linked to the central molecule via any appropriate carbon atom, and when permissible, it may be further substituted.

As used herein, "aryl" refers to any stable mono-cyclic or bi-cyclic carbocycle having up to 7 atoms in each of rings, wherein at least one ring is aromatic. The examples of the above aryl unit include phenyl, naphthyl, tetrahydronaphthyl, 2,3-dihydroindenyl, biphenylyl, phenanthryl, anthryl or acenaphthyl (acenaphthyl). It is to understand that, where the substituent on the aryl is bi-cyclic and one of rings is non-aromatic, linkage is achieved via the aromatic ring.

As used herein, the terms "heteroaryl" refer to a stable mono-cyclic or bi-cyclic ring having up to 7 atoms in each of rings, wherein at least one ring is aromatic and comprises 1-4 heteroatoms selected from O, N and S. The heteroaryl within the definition includes, but not limited to: acridinyl, carbazolyl, cinnolinyl, quinoxalyl, pyrazolyl, indolyl, benzotriazolyl, furanyl, thienyl, benzothiophenyl, benzofuranyl, quinolyl, isoquinolyl, oxazolyl, iso-oxazolyl, indolyl, pyrazinyl, pyridazinyl, pyridyl, pyrimidinyl, pyrrolyl, and tetrahydroquinoline. As in the following definition of heterocycle, "heteroaryl" is further construed to include N-oxide derivatives of any nitrogen-containing heteroaryl. Where the substituent on the heteroaryl is bi-cyclic and one of rings is non-aromatic or does not comprise heteroatom, it is understood that linkage is achieved via the aromatic ring or heteroatom-containing ring, respectively.

As used herein, the terms "heterocyclic ring" or "heterocyclic radical" refer to a 5-10-membered aromatic or non-aromatic heterocyclic ring comprising 1-4 heteroatoms selected from O, N and S, and include bi-cyclic radical. Therefore, "heterocyclic radical" includes the above heteroaryl and dihydro or tetrohydro analogs thereof. The other examples of "heterocyclic radical" include, but not limited to: benzimidazolyl, benzofuranyl, benzofurazanyl, benzopyrazolyl, benzotriazolyl, benzothiophenyl, benzooxazolyl, carbazolyl, carbolinyl, cinnolinyl, furanyl, imidazolyl, dihydroindolyl, indolyl, indazolyl, isobenzofuranyl, isoazaindene, isoquinolyl, isothiazolyl, iso-oxazolyl, naphthopyrimidinyl, oxadiazolyl, oxazolyl, oxazoline, isooxazoline, oxetanyl, pyranyl, pyrazinyl, pyrazolyl, pyridazinyl, pyridopyridinyl, pyridazinyl, pyridyl, pyrimidinyl, pyrrolyl, quinazolinyl, quinolyl, quinoxalyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisoxazolyl, dihydroisothiazolyl, dihydrooxadiazolyl, dihydroxazolyl, dihydropyrazinyl, dihydropyrazolyl, dihydroquinolyl, dihydrotetrazolyl, dihydrothiadizolyl, dihydrothienyl, dihydrotriazolyl, dihydroazetidinyl, methylenedioxybenzoyl, tetrahydrofuranyl and tetrahydrothienyl, and N-oxides thereof. The substituent on the heterocyclic radical may be linked via carbon atom or heteroatom.

In the present invention, the pharmaceutically acceptable salts are preferably the acid addition salts prepared from the compounds of the present invention and the pharmaceutically acceptable acids, or those from reaction of the compounds having the acid group with the basic compounds. Among others, the acids are preferably selected from mineral acids (such as hydrochloric acid, sulfuric acid, phosphoric acid or hydrobromic acid etc.), and organic acids (such as oxalic acid, maleic acid, fumaric acid, malic acid, tartaric acid, citric acid or benzoic acid etc.); the basic compounds are preferably selected from sodium hydroxide, potassium hydroxide, calcium hydroxide, sodium carbonate or potassium bicarbonate etc. The pharmaceutically acceptable salts are susceptible to separation, and may be purified by conventional separation methods, such as extraction into solvent, dilution, recrystallization, column chromatography and preparative thin-layer chromatography.

The second object of the present invention is to provide two methods for preparing the compounds represented by formula I or pharmaceutically acceptable salts thereof.

Method (1):

The method for preparing the compounds represented by formula I or pharmaceutically acceptable salts thereof,

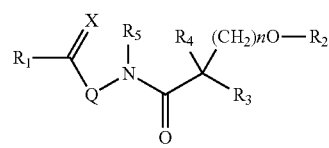

wherein $R_1$, $R_2$, $R_3$, $R_4$, $R_5$, $R_6$, $R_7$, $R_8$, Q, X, m and n are as described above;

includes a step of direct condensation between the acid represented by III and the amine compounds represented by IV at the presence of a condensation agent and solvent, with equation as follows:

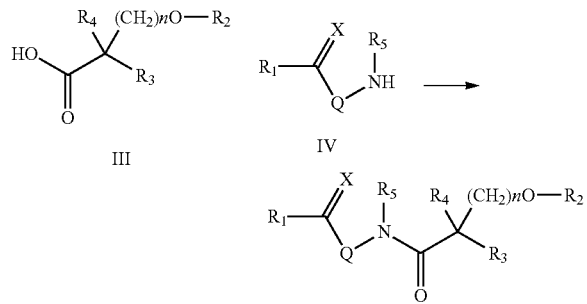

In a preferred embodiment according to the present invention, the condensation agent is the conventional ester condensation agent, such as N,N'-carbonyldiimidazole, dicyclohexylcarbodiimide, and diisopropylcarbodiimide.

In a preferred embodiment according to the present invention, the solvent is selected from the halohydrocarbons, such as dichloromethane, dichloroethane and chloroform; and the ester solvents, such as ethyl acetate and isopropyl acetate.

In a preferred embodiment according to the present invention, the nitrogen-containing catalysts, such as N,N-dimethylaminopyridine, may be added to the reaction for acceleration of reaction rate.

Method (2):

The method for preparing the compounds represented by formula I or pharmaceutically acceptable salts thereof,

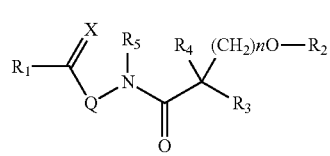

wherein $R_1$, $R_2$, $R_3$, $R_4$, $R_5$, $R_6$, $R_7$, $R_8$, Q, X, m and n are as described above;

includes the following steps: 1) reaction of the acid represented by III with the halogenation reagent to give the acyl halide V; 2) further condensation of V and the amine compounds represented by IV in the solvent, with equation as follows:

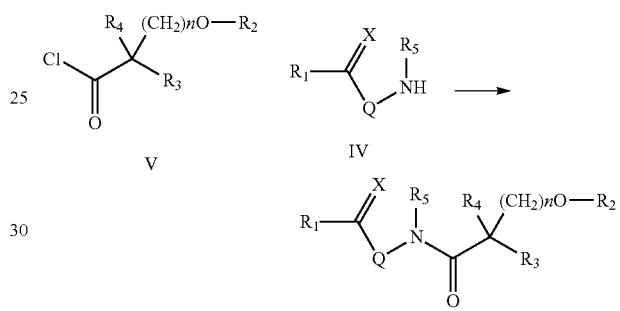

In a preferred embodiment according to the present invention, the halogenation reagent includes oxalyl chloride, thionyl chloride, phosphorus trichloride, phosphorous pentachloride, thionyl bromide, phosphorus tribromide, etc.

In a preferred embodiment according to the present invention, the solvent is selected from the halohydrocarbons, such as dichloromethane, dichloroethane and chloroform; and the ester solvents, such as ethyl acetate and isopropyl acetate.

In a preferred embodiment according to the present invention, the inorganic bases such as sodium hydroxide, potassium hydroxide, sodium carbonate and potassium carbonate; and the organic bases such as triethylamine and pyridine may be added to condensation reaction for acceleration of reaction rate.

The third object of the present invention is to provide a pharmaceutical composition comprising the compound represented by formula I or pharmaceutically acceptable salts thereof and pharmaceutically acceptable additives.

The compounds of the present invention may be used with a variety of pharmaceutically available additives (such as diluent and excipient) to prepare pharmaceutical composition. For treatment purpose, the pharmaceutical composition may formulated into various types of unit dosage form, such as tablet, pill, powder, liquid, suspension, emulsion, granule, capsule, suppository and ampoule (solution and suspension).

For preparing the pharmaceutical composition in the form of tablet, any of excipients extensively used and known in the art may be used, for example carriers, such as lactose, white sugar, sodium chloride, glucose, urea, starch, calcium carbonate, kaolin, crystalline cellulose and silicic acid; adhesives, such as water, ethyl alcohol, propyl alcohol, common syrup, glucose solution, starch solution, gelatin solution, carboxymethyl cellulose, shellac, methyl cellulose and potassium phosphate, polyvinyl pyrrolidone; disintegrant, such as dry starch, sodium alginate, agar powder and seaweed powder, sodium bicarbonate, calcium carbonate, polyethylene sorbitan fatty acid ester, sodium dodecyl sulfate, mono-glycerol stearate, starch and lactose; disintegration inhibitors, such as white sugar, glycerol tristearate, coconut oil and hydrogenated oil; adsorption accelerants, such as quaternary ammonium base and sodium dodecyl sulfate; wetting agents, such as glycerol and starch; adsorbent, such as starch, lactose, kaolin, bentonite and colloid silicic acid; and lubricants, such as neat talcum, stearate, boric acid powder and polyethylene glycol. If required, tablet may also be used with the common coating materials as sugar-coated tablet, gelatin-coated tablet, enteric-coated tablet, film-coated tablet, bifilm-coated tablet and multilayer tablet.

For preparing the pharmaceutical composition in the form of pill, any of excipients extensively used and known in the art may be used, for example, carriers, such as lactose, starch, coconut oil, vegetable tallow, kaolin and talcum; adhesives, such as gum arabic powder, gum tragacanth powder, gelatin and ethyl alcohol; disintegrant, such as agar and seaweed powder.

For preparing the pharmaceutical composition in the form of suppository, any of the excipients extensively used and known in the art may be used, such as polyethylene glycol, coconut oil, higher alcohols, esters of higher alcohols, gelatin and semisynthetic glyceride.

For preparing the pharmaceutical composition in the form of ampoule, the solution and suspension are sterilized and an appropriate amount of sodium chloride, glucose or glycerol etc. is added to it, to give the ampoule having isotonia with blood. For preparation of ampoule, any of carriers commonly used in the art may also be used, for example water, ethyl alcohol, propylene glycol, oxyethylated isostearyl alcohol, polyalkoxylated isostearyl alcohol, and fatty acid esters of polyethylene sorbitan. In addition, the conventional dissolving agent, buffering agent and analgesic may also be added. According to need of formulation, colorant, preservatives, flavors, flavoring agent, aromatizer and other agent may also be added.

The content of the compounds represented by formula I or pharmaceutically acceptable salts thereof in the pharmaceutical composition of the present invention is not particularly limited, and may be selected within very broad limits, usually 1-70% by mass, and preferably 1-30% by mass.

In the present invention, administration of the pharmaceutical composition is not particularly limited. The formulation may be selected from various dosage forms for administration, depending on age, sex of patients and other conditions and symptoms. For example, the tablet, pill, solution, suspension, emulsion, granule and capsule are dosed orally; the ampoule is dosed alone, or mixed with a delivering solution for injection (such as glucose solution and amino acid solution) for intravenous injection, and if necessary, the single ampoule may be used for intramuscular, intracutaneous, subcutaneous or intraperitoneal injection; and the suppository is administered to recta.

In the present invention, the dosage may be properly selected, depending on dosing approach, age, sex of patients, and other conditions and symptoms. The usual dosage may be about 0.1-300 mg pharmaceutically active component per kg weight per day. In general, each of unit dosage forms may contain 1-200 mg pharmaceutically active component.

The fourth object of the present invention is to provide the use of the compound represented by formula I or pharmaceutically acceptable salts thereof in the preparation of medicaments for regulating blood lipid and/or preventing gallstone. It is shown in study that, the compounds of the present invention have the effects of reduction of cholesterol and low-density lipoprotein in blood, promotion of choleresis, reduction of cholesterol in the bile, and improvement of bile acid, resulting in prevention from cholelithiasis. The compounds not only have the effects of reduction of triglyceride level in the animal model of hyperlipoidemia, but also the effects of favorable reduction of cholesterol and low-density lipoprotein, and prevention from gallstone in the gallstone model of golden hamster. It is especially important that the compounds provided by the present invention are low in toxicity.

DETAILED DESCRIPTION OF THE INVENTION

Experiment 1

Preparation of Compound 01

1 g of 2-(4-(2-(4-chlorobenzamido)ethyl)phenoxy)-2-methylpropanoic acid, 0.57 g of dicyclohexylcarbodiimide, 0.5 g of 2-amino-1-(4-hydroxyphenyl)ethyl ketone and 60 ml of dichloromethane were placed into a 100 ml single-neck flask, reacted for 4 hours at room temperature, evaporated to dryness, then purified through chromatography on silica gel column, to give the target compound (820 mg). MS (ESI): 495 (M+H$^+$). $^1$H-NMR: 7.720-7.698 (2H, d), 7.629 (1H, s), 7.605-7.584 (2H, d), 7.281 (1H, s), 7.232-7.210 (2H, d), 7.158 (1H, s), 7.011-6.99 (2H, d), 6.810-6.751 (4H, m), 4.559-4.547 (2H, s), 3.484-3.473 (2H, m), 2.764-2.729 (2H, m), 1.381 (6H, s).

Experiment 2

Preparation of Compound 02

2 g of 2-(4-(2-(4-chlorobenzamido)ethyl)phenoxy)-2-methylpropanoic acid, 1.2 g of dicyclohexylcarbodiimide, 0.5 g of 2-amino-1-(4-hydroxyphenyl)ethyl ketone and 60 ml of dichloromethane were placed into the 100 ml single-neck flask, reacted for 4 hours at room temperature, evaporated to dryness, then purified through chromatography on silica gel column, to give the target compound (1.3 g). MS (ESI): 838(M+H$^+$).

Experiment 3

Preparation of Compound 03

1 g of 2-methyl-2-(4-(4-chlorobenzoyl)phenoxy)propanoic acid, 0.57 g of dicyclohexylcarbodiimide, 0.5 g of 2-amino-1-(4-hydroxyphenyl)ethyl ketone and 60 ml of dichloromethane were placed into the 100 ml single-neck flask, reacted for 4 hours at room temperature, evaporated to dryness, then purified through chromatography on silica gel column, to give the target compound (820 mg). MS (ESI): 452 (M+H$^+$). $^1$H-NMR: 7.8-7.85 (2H, d), 7.7-7.8 (4H, m), 7.6(1H, m), 7.42-7.53 (2H, d), 7.04-7.13 (2H, d), 6.9-7, 1 (214, d), 6.84 (1H, s), 4.7 (2H, d), 1.65 (6H, s).

Experiment 4

Preparation of Compound 04

2 g of 2-methyl-2-(4-(4-chlorobenzoyl)phenoxy)propanoic acid, 1.2 g of dicyclohexylcarbodiimide, 0.5 g of 2-amino-1-(4-hydroxyphenyl)ethyl ketone and 60 ml of dichloromethane were placed into the 100 ml single-neck flask, reacted for 4 hours at room temperature, evaporated to dryness, then purified through chromatography on silica gel column, to give the target compound (1.32 g). MS (ESI): 752(M+H$^+$).

Experiment 5

Preparation of Compound 05

1 g of 2,2-dimethyl-5-(2,5-dimethylphenoxy)pentanoic acid, 0.57 g of dicyclohexylcarbodiimide, 0.5 g of 2-amino-1-(4-hydroxyphenyl)ethyl ketone and 60 ml of dichloromethane were placed into the 100 ml single-neck flask, reacted for 4 hours at room temperature, evaporated to dryness, then purified through chromatography on silica gel column, to give the target compound (720 mg). MS (ESI): 384 (M+H$^+$). $^1$H-NMR: 8.017 (1H, s), 7.815-7.794 (1H, d), 6.992-6.914 (4H, m), 6.651-6.595 (3H, m), 4.625-4.614 (2H, d), 3.939-3.910 (2H, m), 2.954 (3H, s), 2.887 (3H, s), 1.778-1.732 (4H, m), 1.272 (6H, s).

Experiment 6

Preparation of Compound 06

2 g of 2,2-dimethyl-5-(2,5-dimethylphenoxy)pentanoic acid, 1.2 g of dicyclohexylcarbodiimide, 0.5 g of 2-amino-1-(4-hydroxyphenyl)ethyl ketone and 60 ml of dichloromethane were placed into the 100 ml single-neck flask, reacted for 4 hours at room temperature, evaporated to dryness, then purified through chromatography on silica gel column, to give the target compound (1.2 g). MS (ESI): 616 (M+H$^+$).

Experiment 7

Preparation of Compound 07

1 g of 2-(4-(2,2-dichlorocyclopropyl)phenoxy)-2-methylpropanoic acid, 0.57 g of dicyclohexylcarbodiimide, 0.5 g of 2-amino-1-(4-hydroxyphenyl)ethyl ketone and 60 ml of dichloromethane were placed into the 100 ml single-neck flask, reacted for 4 hours at room temperature, evaporated to dryness, then purified through chromatography on silica gel column, to give the target compound (760 mg). MS (ESI): 422 (M+H$^+$). $^1$H-NMR: 7.899-7.877 (1H, d), 7.720 (1H, s), 7.167-7.147 (4H, m), 6.992-6.892 (4H, m), 4.732-4.711 (2H, d), 1.953 (1H, m), 1.554 (6H, s), 1.225 (2H, m).

Experiment 8

Preparation of Compound 08

2 g of 2-(4-(2,2-dichlorocyclopropyl)phenoxy)-2-methylpropanoic acid, 1.2 g of dicyclohexylcarbodiimide, 0.6 g of 2-amino-1-(4-hydroxyphenyl)ethyl ketone and 60 ml of dichloromethane were placed into the 100 ml single-neck flask, reacted for 4 hours at room temperature, evaporated to dryness, then purified through chromatography on silica gel column, to give the target compound (1.15 g). MS (ESI): 694 (M+H$^+$). $^1$H-NMR: 8.085-8.064 (1H, d), 7.987-7.967 (2H, d), 7.169-7.026 (6H, m), 6.982-6.916 (4H, m), 4.764-4.753 (2H, d), 2.866-2.820 (2H, m), 1.755 (12H, m), 1.599-1.437 (4H, m).

Experiment 9

Preparation of Compound 09

2 g of 2-(4-chlorophenoxy)-2-methylpropanoic acid, 2.11 g of dicyclohexylcarbodiimide, 1.4 g of 2-amino-1-(4-hydroxyphenyl)ethyl ketone and 60 ml of dichloromethane were placed into the 100 ml single-neck flask, reacted for 4 hours at room temperature, evaporated to dryness, then purified through chromatography on silica gel column, to give the target compound (2.89 g). MS (ESI): 334 (M+H$^+$).

Experiment 10

Preparation of Compound 10

4 g of 2-(4-chlorophenoxy)-2-methylpropanoic acid, 4.45 g of dicyclohexylcarbodiimide, 1.4 g of 2-amino-1-(4-hydroxyphenyl)ethyl ketone and 60 ml of dichloromethane were placed into the 100 ml single-neck flask, reacted for 4 hours at room temperature, evaporated to dryness, then purified through chromatography on silica gel column, to give the target compound (5.11 g). MS (ESI): 530 (M+H$^+$).

Experiment 11

Preparation of Compound 11

2 g of 2,2'-(cyclohexylidene-bis(p-phenyleneoxy))bis(2-methylbutyric acid), 1.2 g of dicyclohexylcarbodiimide, 0.6 g of 2-amino-1-(4-hydroxyphenyl)ethyl ketone and 60 ml of dichloromethane were placed into the 100 ml single-neck flask, reacted for 4 hours at room temperature, evaporated to dryness, then purified through chromatography on silica gel column, to give the target compound (2.16 g). MS (ESI): 588 (M+H$^+$).

Experiment 12

Preparation of Compound 12

4 g of 2,2'-(cyclohexylidene-bis(p-phenyleneoxy))bis(2-methylbutyric acid), 2.48 g of dicyclohexylcarbodiimide, 0.6 g of 2-amino-1-(4-hydroxyphenyl)ethyl ketone and 60 ml of dichloromethane were placed into the 100 ml single-neck flask, reacted for 4 hours at room temperature, evaporated to dryness, then purified through chromatography on silica gel column, to give the target compound (3.56 g). MS (ESI): 707 (M+H$^+$).

Experiment 13

Preparation of Compound 13

2 g of 2,2-diethyl-5-(3,5-dimethylphenoxy)pentanoic acid, 1.9 g of dicyclohexylcarbodiimide, 1.1 g of 2-amino-1-(3-hydroxyphenyl)ethyl ketone and 60 ml of dichloromethane were placed into the 100 ml single-neck flask, reacted for 4 hours at room temperature, evaporated to dryness, then purified through recrystallization in ethyl alcohol, to give the title compound (2.88 g). MS (ESI): 412 (M+H$^+$).

Experiment 14

Preparation of Compound 14

2 g of 2,2-dimethyl-5-(3-methyl-4-methoxyphenoxy)pentanoic acid, 1.8 g of dicyclohexylcarbodiimide, 1.2 g of 2-amino-1-(3-methyl-4-hydroxyphenyl)ethyl ketone and 60 ml of dichloromethane were placed into the 100 ml single-neck flask, reacted for 4 hours at room temperature, evaporated to dryness, then purified through recrystallization in ethyl alcohol, to give the title compound (2.78 g). MS (EST): 414 (M+H$^+$).

Experiment 15

Preparation of Compound 15

2 g of 2-methyl-2-isopropyl-5-(3-chloro,6-methylphenoxy)pentanoic acid, 1.7 g of dicyclohexylcarbodiimide, 1.1 g of 3-amino-1-(4-hydroxyphenyl)propyl ketone and 60 ml of dichloromethane were placed into the 100 ml single-neck flask, reacted for 4 hours at room temperature, evaporated to dryness, then purified through chromatography on silica gel column, to give the title compound (2.03 g). MS (ESI): 461 (M+H$^+$).

Experiment 16

Preparation of Compound 16

2 g of 2-ethyl-4-(2,5-dimethylphenoxy)butyric acid, 1.7 g of dicyclohexylcarbodiimide, 1.1 g of 2-methyl-2-amino-1-(3-hydroxy-5-methoxyphenyl)ethyl ketone and 60 ml of dichloromethane were placed into the 100 ml single-neck flask, reacted for 4 hours at room temperature, evaporated to dryness, then purified through chromatography on silica gel column, to give the title compound (2.03 g). MS (EST): 412 (M+H$^+$).

Experiment 17

Preparation of Compound 17

2 g of 2,2-dimethyl-5-(2,5-dimethylphenoxy)pentanoic acid, 1.7 g of dicyclohexylcarbodiimide, 1.1 g of 2-methyl-2-amino-1-(3-chloro-4-hydroxyphenyl)ethyl ketone and 60 ml of dichloromethane were placed into the 100 ml single-neck flask, reacted for 4 hours at room temperature, evaporated to dryness, then purified through column chromatography; the product was refluxed for 30 minutes in 5 g butyric acid and ammonia gas, washed with water and 1 mold, sodium hydroxide in water, and the crude product obtained was purified through chromatography on silica gel column, to give the title compound (2.03 g). MS (EST): 433 (M+H$^+$).

Experiment 18

Preparation of Compound 18

2 g of 2,2-dimethyl-5-(2,5-dimethylphenoxy)pentanoic acid, 1.5 g of oxalyl chloride and 10 ml of dichloromethane were placed into the 50 ml single-neck flask for about 1 hour until no gas evolved, and were evaporated to dryness, to give the light yellow oil for use. 1.1 g of (4-aminocyclopropyl)(4-hydroxyphenyl)methylthioketone and 60 ml dichloromethane were placed into the 100 ml single-neck flask, and the oil was dropped slowly into it, reacted for 1 hour at room temperature, evaporated to dryness, then purified through chromatography on silica gel column, to give the title compound (1.1 g). MS (ESI): 468 (M+H$^+$).

Experiment 19

Preparation of Compound 19

1 g of 2,2-dimethyl-5-(2,5-dimethylphenoxy)pentanoic acid, 0.57 g of dicyclohexylcarbodiimide, 0.5 g of 2-amino-1-(3,5-dihydroxyphenyl)ethyl ketone and 60 ml of dichloromethane were placed into the 100 ml single-neck flask, reacted for 4 hours at room temperature, evaporated to dryness, then purified through chromatography on silica gel column, to give the target compound (725 mg). MS (ESI): 400 (M+H$^+$).

Experiment 20

Preparation of Compound 20

1 g of 2-(4-chlorophenyl)-2-cyclopropylpropanoic acid, 0.57 g of dicyclohexylcarbodiimide, 0.5 g of 2-amino-1-(4-hydroxyphenyl)ethyl ketone and 60 ml of dichloromethane were placed into the 100 ml single-neck flask, reacted for 4 hours at room temperature, evaporated to dryness, then purified through chromatography on silica gel column, to give the target compound (500 mg). MS (ESI): 374 (M+H$^+$).

Experiment 21

Preparation of Compound 21

1 g of 2,2-dimethyl-5-(2,5-dimethylphenoxy)pentanoic acid, 0.57 g of dicyclohexylcarbodiimide, 0.5 g of 2-amino-1-(4-hydroxymethylphenyl)ethyl ketone and 60 ml of dichloromethane were placed into the 100 ml single-neck flask, reacted for 4 hours at room temperature, evaporated to dryness, then purified through chromatography on silica gel column, to give the target compound (723 mg). MS (ESI): 398 (M+H$^+$).

Experiment 22

Materials and Methods for Screening with the Compounds Prepared in Experiment 1 to 21 in the Hyperlipemia Model of SD Rat 1. Reagents Simvastatin tablet (20 mg*7, Hangzhou MSD Pharmaceutical Co., Ltd. Lot: 20090115);
Ursodesoxycholic acid (Bio Basic Inc., Lot: YY0201B207Y);
Lard oil: commercially available;
Cholesterol (Shanghai Lanji Sci-tech Development Co., Ltd. Lot: 090720);
Propylthiouracil (Shanghai Lanji Sci-tech Development Co., Ltd. Lot: 090505);
Deoxycholic acid (Shanghai Lanji Sci-tech Development Co., Ltd. Lot: 090615);
Tween 80 (Sinopharm Chemical Reagent Co., Ltd. CP, Lot: F20090507);
1,2-propylene glycol (Sinopharm Chemical Reagent Co., Ltd. AR, Lot: T20070125);

2. Animals

SD rats, male, 150-180 g, supplied by Shanghai Slaccas Laboratory Animal Company Limited.

3. Instruments

YP2001N electronic balance, from Shanghai Precision Scientific Instrument Co., Ltd.

Hitachi Automatic Biochemical Analyzer 7080.

4. Methods

Preparation of fat emulsion: 500 g lard oil was weighed and placed into a vessel, heated for melting, and upon heating up to the temperature of 100° C., 200 g cholesterol was added and fully dissolved, then 20 g propylthiouracil was added. After full stirring and dissolving, 500 ml Tween 80 was added to give an oil phase. Meanwhile, 600 ml distilled water and 400 ml 1,2-propylene glycol were heated to 60° C. in water bath, and then 40 g sodium deoxycholate was added with stirring, until full dissolution, to give an aqueous phase. The aqueous phase was added into the oil phase and fully and uniformly mixed, to prepare the fat emulsion.

Formulation of the solution for the compounds: an appropriate amount of compounds was triturated with appropriate amount of Tween 80 for homogeneous dispersion, and then sufficient CMC-Na solution was added and fully triturated, suspended to give the solution for the compounds.

The animals were fed for acclimation for 3 days, with 8 animals as blank control (Control) according to weight, and the rest was subject to intragastric administration of fat emulsion at 1 ml/100 g weight at A.M. 9:00-11:00 daily for continuous 2 weeks; the animals were fasted for 12 hours, and had 1 ml blood sampled at orbital cavity, which was measured with the Hitachi Automatic Biochemical Analyzer 7080 for serum cholesterol (CHO), triglyceride (TO), low-density lipoprotein (LDL-C) and high-density lipoprotein (HDL-C), with the animals having CHO of 4-7 mmol/L for experiment.

The animals dosed with fat emulsion for 2 weeks were divided into model group (Model), simvastatin group (Sim, 10 mg/kg) and compound group (40 mg/kg) according to weight, and continued to receive intragastric administration with fat emulsion; at the same time, the dosed group was administered with respective amount of drug, and the model group was administered with equal volume of solvent. Fat emulsion was dosed by gavage at A.M., and drug was dosed at P.M. The animals were weighed at Monday, and were observed. The animals were dosed for continuous 21 days, and fasted for 12 hours, with 1 ml blood sampling at orbital cavity. The liver was exposed and observed for pathologic condition; after slicing and weighing, it was fixed into the 4% formaldehyde solution for pathologic examination.

The Hitachi Automatic Biochemical Analyzer 7080 was used to measure serum cholesterol (CHO), triglyceride (TG), low-density lipoprotein (LDL-C) and high-density lipoprotein (HDL-C).

5. Data Statistics

Laboratory data were expressed as X±SD (Standard Deviation), and comparison between groups was carried out by t-testing.

6. Results: Effect of the Compounds on Blood Lipid in Animal

TABLE 1

| Grouping | Dose (mg/kg) | CHO1 Concentration | TG Concentration | HDL-C Concentration | LDL-C Concentration |
|---|---|---|---|---|---|
| Blank (healthy) |  | 1.82 ± 0.34 | 0.44 ± 0.13 | 1.22 ± 0.25 | 0.36 ± 0.08 |
| Model |  | 19.17 ± .315 | 1.95 ± 0.21 | 1.82 ± 0.33 | 18.01 ± 2.76 |
| Simvastatin | 10 | 12.52 ± 1.34 | 1.41 ± 0.16 | 1.52 ± 0.32 | 11.92 ± 1.44 |
| Compound 01 | 40 | 14.84 ± 1.06 | 0.66 ± 0.13 | 1.56 ± 0.25 | 13.90 ± 1.23 |
| Compound 02 | 40 | 17.29 ± 3.23 | 0.68 ± 0.18 | 1.68 ± 0.38 | 16.01 ± 2.99 |
| Compound 03 | 40 | 12.63 ± 2.77 | 0.99 ± 0.18 | 1.54 ± 0.20 | 11.11 ± 2.45 |
| Compound 04 | 40 | 10.02 ± 1.80 | 1.15 ± 0.12 | 1.82 ± 0.19 | 9.84 ± 1.37 |
| Compound 05 | 40 | 15.30 ± 2.45 | 1.31 ± 0.15 | 1.54 ± 0.24 | 14.38 ± 2.12 |
| Compound 06 | 40 | 16.37 ± 2.26 | 1.53 ± 0.16 | 1.49 ± 0.29 | 15.78 ± 2.00 |
| Compound 07 | 40 | 14.99 ± 1.45 | 1.39 ± 0.16 | 1.74 ± 0.46 | 13.90 ± 1.21 |
| Compound 08 | 40 | 12.92 ± 2.10 | 0.83 ± 0.13 | 2.12 ± 0.27 | 11.41 ± 1.90 |
| Compound 09 | 40 | 13.64 ± 2.14 | 0.95 ± 0.14 | 2.18 ± 0.22 | 11.64 ± 2.00 |
| Compound 10 | 40 | 9.73 ± 1.79 | 0.94 ± 0.15 | 2.66 ± 0.24 | 8.27 ± 1.46 |
| Compound 11 | 40 | 12.18 ± 3.12 | 1.13 ± 0.14 | 1.79 ± 0.34 | 11.37 ± 3.66 |
| Compound 12 | 40 | 20.17 ± 1.27 | 0.75 ± 0.25 | 1.895 ± 0.39 | 19.31 ± 1.52 |
| Compound 13 | 40 | 20.17 ± 1.27 | 0.75 ± 0.25 | 1.895 ± 0.39 | 19.31 ± 1.52 |
| Compound 14 | 40 | 20.66 ± 3.23 | 0.99 ± 0.28 | 2.25 ± 0.22 | 20.78 ± 3.46 |
| Compound 15 | 40 | 15.00 ± 2.75 | 1.34 ± 0.48 | 1.89 ± 0.26 | 14.04 ± 3.12 |
| Compound 16 | 40 | 9.48 ± 1.27 | 0.78 ± 0.25 | 1.32 ± 0.39 | 7.13 ± 1.52 |
| Compound 17 | 40 | 10.54 ± 3.23 | 0.88 ± 0.28 | 1.82 ± 0.22 | 8.13 ± 3.46 |
| Compound 18 | 40 | 15.04 ± 2.73 | 1.25 ± 0.33 | 1.56 ± 0.51 | 13.47 ± 3.68 |
| Compound 19 | 40 | 11.12 ± 1.01 | 0.94 ± 0.06 | 1.36 ± 0.66 | 10.76 ± 1.25 |
| Compound 20 | 40 | 19.88 ± 0.84 | 1.72 ± 0.26 | 2.63 ± 0.57 | 18.48 ± 0.43 |
| Compound 21 | 40 | 14.42 ± 2.75 | 2.00 ± 0.52 | 1.69 ± 0.26 | 12.15 ± 3.12 | blood lipid level in the dosed rats (X ± SD, mmol/L)

From the results, the compound 01 to compound 21 substantially have a certain blood lipid-lowering action, while enable reduction of cholesterol, triglyceride and low-density lipoprotein.

Experiment 23

Screening with the Compounds Prepared in Experiment 1 to 21 in the Cholelithiasis Model of Golden Hamster Materials and Methods 1. Reagents:

Simvastatin tablet (20 mg*7, Hangzhou MSD Pharmaceutical Co., Ltd. Lot: 20090115)

Ursodesoxycholic acid (Bio Basic Inc., Lot: YY0201B207Y)

2. Animals:

68 male golden hamsters, 50-60 g, supplied by Shanghai Slaccas Laboratory Animal Company Limited.

3. Instruments:

YP2001N electronic balance, from Shanghai Precision Scientific Instrument Co., Ltd.

Hitachi Automatic Biochemical Analyzer 7080.

4. Methods:

The animals were fed for acclimation for 3 days, with 8 animals as blank control (Control) according to weight. The control was dosed with normal rat feedstuff, and the rest was dosed with feedstuff leading to cholelithiasis (sucrose 32.1%, cheese 64.2%, cholesterol 0.2%, salt 3%, vitamin B1 20.1%, concentrated fish liver oil 0.4%). The animals were fed for acclimation for another 7 days, and divided into model group (Model), simvastatin group (Sim, 10 mg/kg), Ursodesoxycholic acid group (UDCA, 40 mg/kg), and compound group, n=6/group.

The Sim group was administered with simvastatin 10 mg/kg, the UDCA group was administered with ursodesoxycholic acid 40 mg/kg, the dosing group was administered with 40 mg/kg drug, with administration all starting at the day of grouping, and at P.M. 2:00-3:00 daily. The animals were weighed at Monday, and observed for hair color, stool, and variation of activation level.

The animals were dosed for continuous 45 days and then fasted for 12 hours; were anesthetized with 30 mg/kg sodium secobarbital via intraperitoneal injection; had 1 ml blood sampled via abdominal aorta; had gallbladder exposed, with an orifice on the gallbladder being clamped by the ophthalmological pliers and bile in the gallbladder being sucked with 1 ml syringe.

5. Biochemical Measurement of Bile:

The Hitachi Automatic Biochemical Analyzer 7080 was used to measure cholesterol (CHO), total total bilirubin (TBIL), total bile acid (TBA) and total protein (TP) in bile.

6. Data Statistics:

Laboratory data was expressed as X±SD, and comparison of measurement data between groups was carried out by t-testing, with non-parametric testing for enumeration data.

Experiment 24

Testing for Acute Toxicity in Mice

The compounds was dissolved into an appropriate amount of Tween-80, and suspended and dispersed uniformly into a given amount of CMC-Na solution, which was administered orally and by gavage at a dose of 5 g/kg, with no toxicity associated with administration being observed, and no death of animals occurred during observation of continuous 14 days. From the results, the sample Compound 01, Compound 02, Compound 03, Compound 04, Compound 05, Compound 06, Compound 07, Compound 08, Compound 09, Compound 10, Compound 11, Compound 12, Compound 13, Compound 14, Compound 15, Compound 16, Compound 17, Compound 18, Compound 19, Compound 20 and Compound 21 were safe.

Experiment 25

Preparation of Tablets

| Formulation | Dosage |
| --- | --- |
| Compound 11 | 200 mg |
| Microcrystalline cellulose | 200 mg |
| Crosslinked Polyvinylpyrrolidone | 20 mg |
| Pregelatinized starch | 50 mg |
| Magnesium stearate | 5 mg |

Preparation method: according to the above formulation, the comminuted and sieved compound 11, microcrystalline cellulose, pre-gelatinized starch and cross-linked polyvinylpyrrolidone were mixed uniformly, and then mixed with 5% ethyl alcohol solution, granulated, dried, and then the granules obtained was mixed with the lubricant and pressed into tablets; wherein the compound 11 was comminuted and sieved through the 60-mesh sieve, the microcrystalline cellulose, pregelatinized starch and crosslinked polyvinylpyr- 7. Laboratory results: Table 2. level of components in golden hamster bile

| Group | Number of animals | Cholesterol (CHO) (mmol/L) | Total total bilirubin (TBIL) (μmol/L) | Total bile acid (TBA) (mmol/L) | Total protein (TP) (g/L) |
| --- | --- | --- | --- | --- | --- |
| Blank (healthy) | 8 | 0.90 ± 0.21 | 68.1 ± 24.2 | 17.44 ± 10.12 | 25.83 ± 11.24 |
| Model | 6 | 1.16 ± 0.72 | 73.8 ± 34.6 | 10.12 ± 5.66 | 37.89 ± 17.23 |
| Simvastatin (10 mg/kg) | 6 | 1.07 ± 0.63 | 79.2 ± 34.2 | 7.68 ± 3.31 | 35.52 ± 18.04 |
| Ursodesoxycholic acid (40 mg/kg) | 6 | 0.98 ± 0.47 | 89.4 ± 45.3 | 12.23 ± 3.04 | 28.63 ± 10.37 |
| Compound 11 (80 mg/kg) | 6 | 0.82 ± 0.58** | 48.9 ± 22.10 | 17.46 ± 7.77** | 28.66 ± 8.48 |
| Compound 16 (40 mg/kg) | 6 | 0.97 ± 0.62** | 55.0 ± 29.38 | 19.74 ± 12.14** | 40.70 ± 26.17 |
| Compound 20 (20 mg/kg) | 6 | 0.92 ± 0.66** | 75.92 ± .072 | 16.80 ± 9.62** | 32.94 ± 19.18 |

**refers to a very significant statistic difference.

From results of bile analysis, the contents of bile acid in each of the compound groups were significantly higher than that in the model group, and were better than that of simvastatin and ursodesoxycholic acid in effect of increased bile acid.

rolidone were comminuted and sieved through the 80-mesh sieve, the granulation gave the particles with particle size of 20 mesh, and the drying was carried out at the temperature of preferable 90° C., and moisture was controlled within 3% by mass.

Experiment 26

Preparation of Capsules

|  | Formulation | Dosage |
| --- | --- | --- |
|  | Compound 16 | 200 mg |
| Filler | Lactose | 250 mg |
| Lubricant | Magnesium stearate | 2 mg |

Preparation method: according to the above formulation, the medicament was mixed uniformly with each of the raw materials as adjuvant, and filled into the capsule shells.

Experiment 27

Preparation of Injection

|  | Raw materials | mg/mL |
| --- | --- | --- |
|  | Compound 02 | 100 |
| Suspending agent | Gum tragacanth | 1.0 |
| Wetting agent | Isopropanol | 1.0 |
|  | Water for injection | Ad. 1 mL |

Preparation method: according to the above formulation, a mortar was used to grind the compound 02 or salt thereof and the wetting agent for uniform mixing, and then mixed uniformly with the suspending agent, preservative and water for injection, and then regrinded, wherein the grinding provided the particle size of 0.5 μm.

What is claimed is:

1. A compound and pharmaceutically acceptable salts thereof, wherein the compound is selected from:

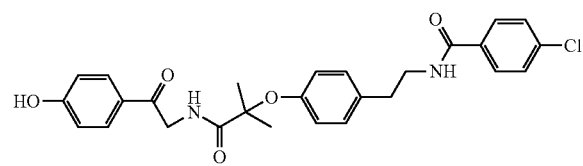

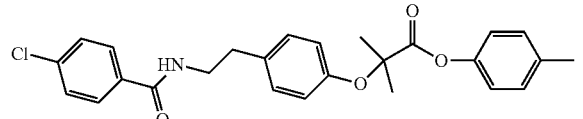

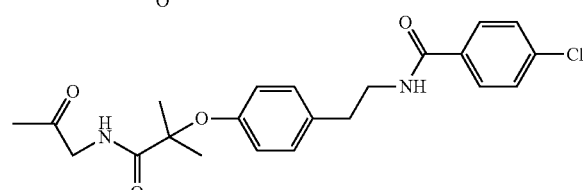

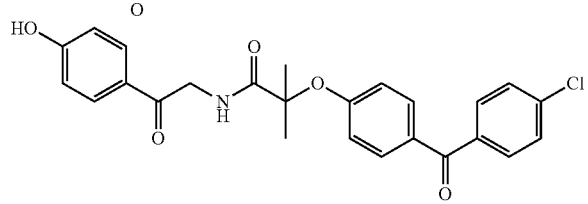

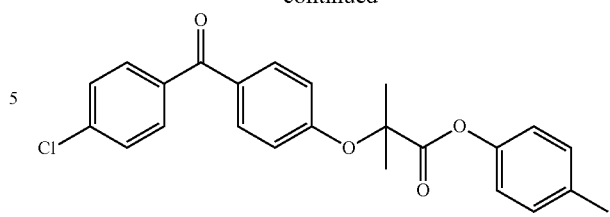

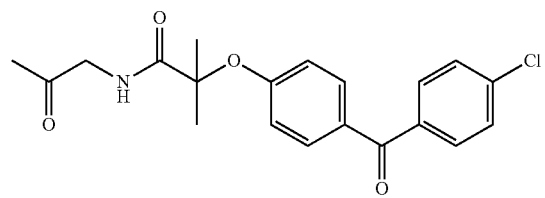

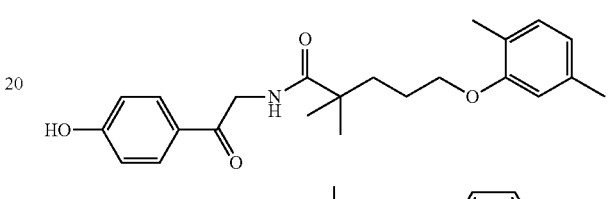

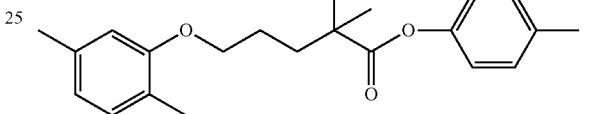

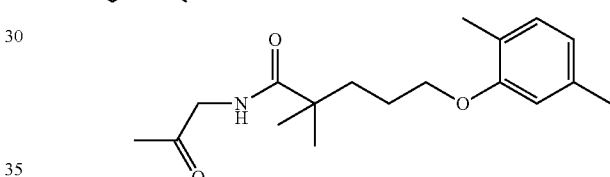

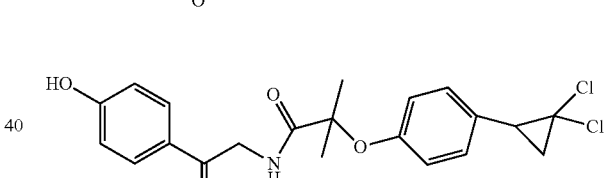

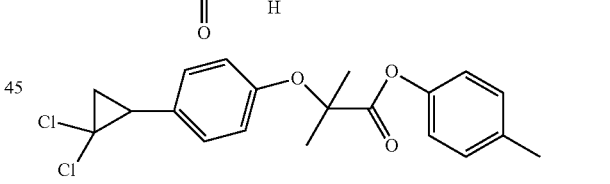

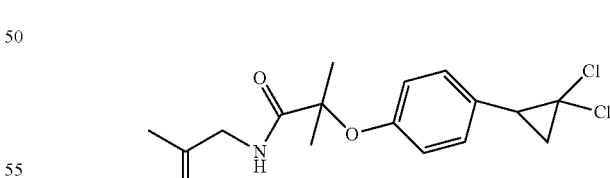

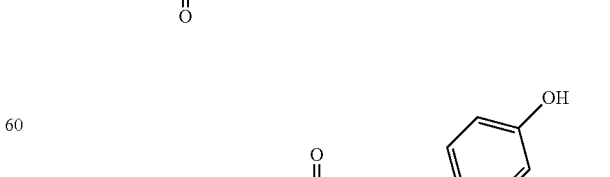

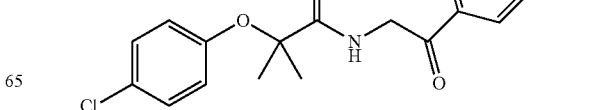

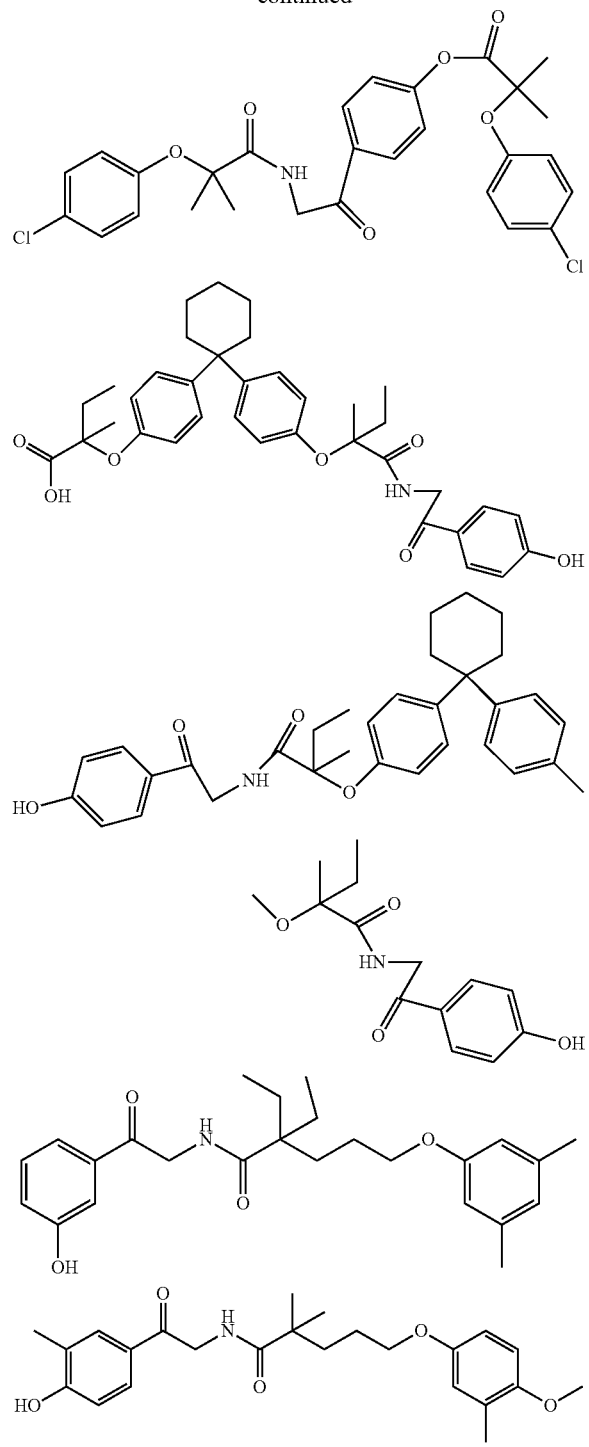
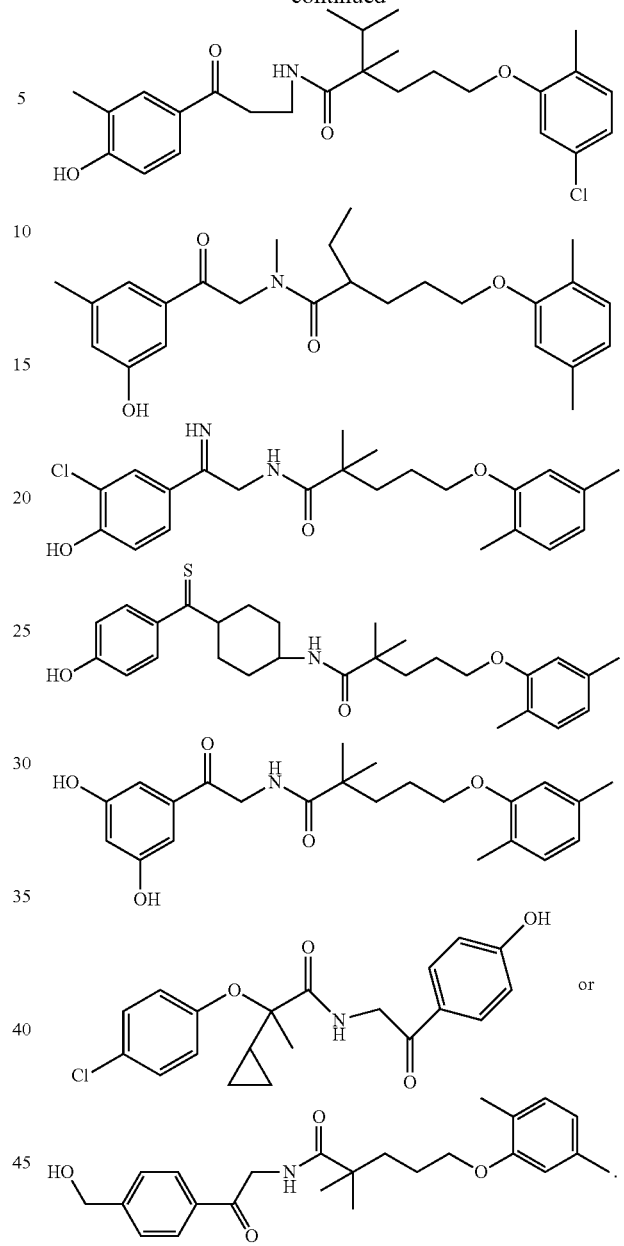
2. A pharmaceutical composition, comprising any one compound of claim 1, and a pharmaceutically acceptable additive.
3. The pharmaceutical composition according to the claim 2, in the form of tablet, pill, powder, liquid, suspension, emulsion, granule, capsule, suppository or ampoule.
* * * * *